United States Patent
Gunji et al.

(10) Patent No.: US 7,217,543 B2
(45) Date of Patent: May 15, 2007

(54) METHOD FOR PRODUCING L-AMINO ACID USING METHYLOTROPH

(75) Inventors: Yoshiya Gunji, Kanagawa (JP); Hisashi Yasueda, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 187 days.

(21) Appl. No.: 10/716,473

(22) Filed: Nov. 20, 2003

(65) Prior Publication Data

US 2004/0142435 A1 Jul. 22, 2004

(30) Foreign Application Priority Data

Nov. 20, 2002 (JP) ............................. 2002-336346

(51) Int. Cl.
*C12P 13/04* (2006.01)

(52) U.S. Cl. ..................... 435/106; 435/7.1; 435/106; 435/69.1; 435/325; 536/23.1

(58) Field of Classification Search ..................... None
See application file for complete search history.

(56) References Cited

U.S. PATENT DOCUMENTS

| | | | |
|---|---|---|---|
| 3,220,929 A | 11/1965 | Kinoshita et al. | 195/29 |
| 3,563,857 A | 2/1971 | Oki et al. | 195/49 |
| 3,907,637 A | 9/1975 | Nakayama et al. | 195/29 |
| 3,907,641 A | 9/1975 | Nakayama et al. | 195/49 |
| 5,217,883 A | 6/1993 | Anazawa et al. | 435/252.3 |
| 5,378,616 A | 1/1995 | Tujimoto et al. | 435/110 |
| 5,393,671 A | 2/1995 | Tujimoto et al. | 435/252.8 |
| 6,461,852 B1 | 10/2002 | Tsujimoto et al. | |
| 2003/0013174 A1 | 1/2003 | Tsujimoto et al. | |
| 2003/0049805 A1 | 3/2003 | Nagase et al. | |
| 2003/0124687 A1 | 7/2003 | Gunji et al. | |
| 2003/0166174 A1 | 9/2003 | Ono et al. | |
| 2003/0232338 A1 | 12/2003 | Usuda et al. | |
| 2004/0146974 A1 | 7/2004 | Gunji et al. | |
| 2004/0166570 A1 | 8/2004 | Yasueda et al. | |
| 2004/0170985 A1 | 9/2004 | Usuda et al. | |
| 2004/0170986 A1 | 9/2004 | Usuda et al. | |
| 2004/0170987 A1 | 9/2004 | Usuda et al. | |
| 2004/0171134 A1 | 9/2004 | Yasueda et al. | |
| 2004/0191875 A1 | 9/2004 | Takeshita et al. | |
| 2004/0214296 A1 | 10/2004 | Asahara et al. | |
| 2004/0229311 A1 | 11/2004 | Hirano et al. | |
| 2005/0003495 A1 | 1/2005 | Gunji et al. | |

FOREIGN PATENT DOCUMENTS

| | | |
|---|---|---|
| EP | 1 188 822 | 3/2002 |
| EP | 1241246 | 9/2002 |
| EP | 1 352 966 | 10/2003 |
| JP | 45-25273 | 8/1970 |
| JP | 50-25790 | 3/1975 |
| JP | 52-18886 | 2/1977 |
| WO | WO90/12105 | 10/1990 |
| WO | WO01/02542 | 1/2001 |
| WO | WO01/02543 | 1/2001 |
| WO | 02/20796 | 3/2002 |

OTHER PUBLICATIONS

U.S. Appl. No. 09/926,299, filed Oct. 9, 2001, Gunji et al.
U.S. Appl. No. 10/791,853, filed Mar. 4, 2004, Takeshita et al.
Hiroshi Aida et al., Amino Acid Fermentation, Kabushiki Kaisha Gakukai Shuppan Center, May 30, 1986, p. 76-100.
Sara E. Egan et al., Molecular Characterization of the Entner-Doudoroff Pathway in *Escherichia coli*: Sequence Analysis and Localization of Promoters for the edd-eda Operon, Journal of Bacteriology, Jul. 1992, p. 4638-4646, vol. 174, No. 14.
Owen Jenkins et al., *Methylophilus*: a New Genus of Methanol-Utilizing Bacteria, International Journal of Systematic Bacteriology, Oct. 1987, p. 446-448, vol. 37, No. 4.
Teizi Urakami et al., Emendation of *Methylobacillus*: Yordy and Weaver 1977, a Genus for Methanol-Utilizing Bacteria, International Journal of Systematic Bacteriology, Oct. 1986, p. 502-511, vol. 36, No. 4.

*Primary Examiner*—Hope Robinson
(74) *Attorney, Agent, or Firm*—Cermak & Kenealy, LLP; Shelly Guest Cermak

(57) ABSTRACT

The present invention describes a method for producing an L-amino acid comprising culturing a microorganism having an ability to produce an L-amino acid in a medium, whereby the L-amino acid accumulates in the medium, and collecting the L-amino acid from the medium, whereby said microorganism comprises a methanol-utilizing bacterium having the Entner-Doudoroff pathway in which 6-phosphogluconate dehydratase activity and/or 2-keto-3-deoxy-6-phosphogluconate aldolase activity is enhanced.

7 Claims, 2 Drawing Sheets

SEQUENCE LISTING

<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 1
agggaattcc ccgttctgga taatgttttt tgcgccgac                    39

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 2
cggatgcatc tagagttaac ctgcagggtg aaattgttat ccgctcacaa ttccacac    58

<210> SEQ ID NO 3
<211> LENGTH: 35
<212> TYPE: DNA
<213> ORGANISM: Artificial Sequence
<220> FEATURE:

```
<223> OTHER INFORMATION: Description of Artificial Sequence: primer

<400> SEQUENCE: 3
tgacctgcag gtttgcacag aggatggccc atgtt                              35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 4
cattctagat ccctaaactt tacagcaaac cggcat                             36

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 5
catttcctgc aggcaaagga gatgagcgta atggtgatca tggaaatctt cattacaggt   60
ctgc                                                                64

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gggcgagcta aagagctcc aaacccgcg aaaactaacc catcaacatc                50

<210> SEQ ID NO 7
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 7
```

| | | | | | | | | | | | | | | | | |
|---|---|---|---|---|---|---|---|---|---|---|---|---|---|---|---|---|
| atg | gtg | atc | atg | gaa | atc | ttc | att | aca | ggt | ctg | ctt | ttg | ggg | gcc | agt | 48 |
| Met | Val | Ile | Met | Glu | Ile | Phe | Ile | Thr | Gly | Leu | Leu | Leu | Gly | Ala | Ser | |
| 1 | | | | 5 | | | | | 10 | | | | | 15 | | |
| ctt | tta | ctg | tcc | atc | gga | ccg | cag | aat | gta | ctg | gtg | att | aaa | caa | gga | 96 |
| Leu | Leu | Leu | Ser | Ile | Gly | Pro | Gln | Asn | Val | Leu | Val | Ile | Lys | Gln | Gly | |
| | | | | 20 | | | | | 25 | | | | | 30 | | |
| att | aag | cgc | gaa | gga | ctc | att | gcg | gtt | ctt | ctc | gtg | tgt | tta | att | tct | 144 |
| Ile | Lys | Arg | Glu | Gly | Leu | Ile | Ala | Val | Leu | Leu | Val | Cys | Leu | Ile | Ser | |
| | | 35 | | | | | 40 | | | | | 45 | | | | |
| gac | gtc | ttt | ttg | ttc | atc | gcc | ggc | acc | ttg | ggc | gtt | gat | ctt | ttg | tcc | 192 |
| Asp | Val | Phe | Leu | Phe | Ile | Ala | Gly | Thr | Leu | Gly | Val | Asp | Leu | Leu | Ser | |
| | 50 | | | | | 55 | | | | | 60 | | | | | |
| aat | gcc | gcg | ccg | atc | gtg | ctc | gat | att | atg | cgc | tgg | ggt | ggc | atc | gct | 240 |
| Asn | Ala | Ala | Pro | Ile | Val | Leu | Asp | Ile | Met | Arg | Trp | Gly | Gly | Ile | Ala | |
| 65 | | | | | 70 | | | | | 75 | | | | | 80 | |
| tac | ctg | tta | tgg | ttt | gcc | gtc | atg | gca | gcg | aaa | gac | gcc | atg | aca | aac | 288 |
| Tyr | Leu | Leu | Trp | Phe | Ala | Val | Met | Ala | Ala | Lys | Asp | Ala | Met | Thr | Asn | |
| | | | | 85 | | | | | 90 | | | | | 95 | | |

| | | | | | | | | | | | | | | | |
|---|---|---|---|---|---|---|---|---|---|---|---|---|---|---|---|
| aag | gtg | gaa | gcg | cca | cag | atc | att | gaa | gaa | aca | gaa | cca | acc | gtg | ccc | 336
| Lys | Val | Glu | Ala | Pro | Gln | Ile | Ile | Glu | Glu | Thr | Glu | Pro | Thr | Val | Pro |
| | | | 100 | | | | | 105 | | | | | 110 | | |

```
aag gtg gaa gcg cca cag atc att gaa gaa aca gaa cca acc gtg ccc    336
Lys Val Glu Ala Pro Gln Ile Ile Glu Glu Thr Glu Pro Thr Val Pro
            100                 105                 110 gat gac acg cct ttg ggc ggt tcg gcg gtg gcc act gac acg cgc aac    384
Asp Asp Thr Pro Leu Gly Gly Ser Ala Val Ala Thr Asp Thr Arg Asn
            115                 120                 125 cgg gtg cgg gtg gag gtg agc gtc gat aag cag cgg gtt tgg gta aag    432
Arg Val Arg Val Glu Val Ser Val Asp Lys Gln Arg Val Trp Val Lys
130                 135                 140 ccc atg ttg atg gca atc gtg ctg acc tgg ttg aac ccg aat gcg tat    480
Pro Met Leu Met Ala Ile Val Leu Thr Trp Leu Asn Pro Asn Ala Tyr
145                 150                 155                 160 ttg gac gcg ttt gtg ttt atc ggc ggc gtc ggc gca caa tac ggc gac    528
Leu Asp Ala Phe Val Phe Ile Gly Gly Val Gly Ala Gln Tyr Gly Asp
                165                 170                 175 acc gga cgg tgg att ttc gcc gct ggc gcg ttc gcg gca agc ctg atc    576
Thr Gly Arg Trp Ile Phe Ala Ala Gly Ala Phe Ala Ala Ser Leu Ile
                180                 185                 190 tgg ttc ccg ctg gtg ggt ttc ggc gca gca gca ttg tca cgc ccg ctg    624
Trp Phe Pro Leu Val Gly Phe Gly Ala Ala Ala Leu Ser Arg Pro Leu
            195                 200                 205 tcc agc ccc aag gtg tgg cgc tgg atc aac gtc gtc gtg gca gtt gtg    672
Ser Ser Pro Lys Val Trp Arg Trp Ile Asn Val Val Val Ala Val Val
210                 215                 220 atg acc gca ttg gcc atc aaa ctg atg ttg atg ggt tag                711
Met Thr Ala Leu Ala Ile Lys Leu Met Leu Met Gly
225                 230                 235

<210> SEQ ID NO 8
<211> LENGTH: 236
<212> TYPE: PRT
<213> ORGANISM: Brevibacterium lactofermentum

<400> SEQUENCE: 8

Met Val Ile Met Glu Ile Phe Ile Thr Gly Leu Leu Leu Gly Ala Ser
 1               5                  10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
        115                 120                 125

Arg Val Arg Val Glu Val Ser Val Asp Lys Gln Arg Val Trp Val Lys
    130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190
```

```
Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Ala Val Val
        210                 215                 220

Met Thr Ala Leu Ala Ile Lys Leu Met Leu Met Gly
225                 230                 235

<210> SEQ ID NO 9
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)

<400> SEQUENCE: 9 atg gtg atc atg gaa atc ttc att aca ggt ctg ctt ttg ggg gcc agt     48
Met Val Ile Met Glu Ile Phe Ile Thr Gly Leu Leu Leu Gly Ala Ser
 1               5                  10                  15 ctt ttg ctg tcc atc gga ccg cag aat gta ctg gtg att aaa caa gga     96
Leu Leu Leu Ser Ile Gly Pro Gln Asn Val Leu Val Ile Lys Gln Gly
             20                  25                  30 att aag cgc gaa gga ctc att gcg gtt ctt ctc gtg tgt tta att tct    144
Ile Lys Arg Glu Gly Leu Ile Ala Val Leu Leu Val Cys Leu Ile Ser
         35                  40                  45 gac gtc ttt ttg ttc atc gcc ggc acc ttg ggc gtt gat ctt ttg tcc    192
Asp Val Phe Leu Phe Ile Ala Gly Thr Leu Gly Val Asp Leu Leu Ser
     50                  55                  60 aat gcc gcg ccg atc gtg ctc gat att atg cgc tgg ggt ggc atc gct    240
Asn Ala Ala Pro Ile Val Leu Asp Ile Met Arg Trp Gly Gly Ile Ala
 65                  70                  75                  80 tac ctg tta tgg ttt gcc gtc atg gca gcg aaa gac gcc atg aca aac    288
Tyr Leu Leu Trp Phe Ala Val Met Ala Ala Lys Asp Ala Met Thr Asn
                 85                  90                  95 aag gtg gaa gcg cca cag atc att gaa gaa aca gaa cca acc gtg ccc    336
Lys Val Glu Ala Pro Gln Ile Ile Glu Glu Thr Glu Pro Thr Val Pro
            100                 105                 110 gat gac acg cct ttg ggc gtg ttc ggc ggt ggc cac tga cacgcgcaac    385
Asp Asp Thr Pro Leu Gly Val Phe Gly Gly Gly His
            115                 120         125 cgggtgcggg tggaggtgag cgtcgataag cagcgggttt gggtgaagcc catgttgatg    445
gcaatcgtgc tgacctggtt gaacccgaat gcgtatttgg acgcgtttgt gtttatcggc    505
ggcgtcggcg cgcaatacgg cgacaccgga cggtggattt tcgccgctgg cgcgttcgcg    565
gcaagcctga tctggttccc gctggtgggt ttcggcgcag cagcattgtc acgcccgctg    625
tccagcccca aggtgtggcg ctggatcaac gtcgtcgtgg cagttgtgat gaccgcattg    685
gccatcaaac tgatgttgat gggttag                                       712

<210> SEQ ID NO 10
<211> LENGTH: 124
<212> TYPE: PRT
<213> ORGANISM: Brevibacterium lactofermentum

<400> SEQUENCE: 10

Met Val Ile Met Glu Ile Phe Ile Thr Gly Leu Leu Leu Gly Ala Ser
 1               5                  10                  15

Leu Leu Leu Ser Ile Gly Pro Gln Asn Val Leu Val Ile Lys Gln Gly
             20                  25                  30
```

```
Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Val Phe Gly Gly Gly His
            115                 120

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 11
cccccgggat tccttcctc cggtctgctt                                          30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 12
taaagcttgg tcaggcgtt ggcggtggcg                                          30

<210> SEQ ID NO 13
<211> LENGTH: 1197
<212> TYPE: DNA
<213> ORGANISM: Escherichia coli
<220> FEATURE:
<221> NAME/KEY: CDS
<222> LOCATION: (272)..(1153)

<400> SEQUENCE: 13
ccaggcgact gtcttcaata ttacagccgc aactactgac atgacgggtg atggtgttca        60
caattccacg gcgatcggca cccaacgcag tgatcaccag ataatgtgtt gcgatgacag       120
tgtcaaactg gttattcctt taagggtga gttgttctta aggaaagcat aaaaaaaaca        180
tgcatacaac aatcagaacg ttctgtctg cttgctttta atgccatacc aaacgtacca       240
ttgagacact tgtttgcaca gaggatggcc c atg ttc acg gga agt att gtc          292
                                   Met Phe Thr Gly Ser Ile Val
                                     1               5 gcg att gtt act ccg atg gat gaa aaa ggt aat gtc tgt cgg gct agc          340
Ala Ile Val Thr Pro Met Asp Glu Lys Gly Asn Val Cys Arg Ala Ser
         10                  15                  20 ttg aaa aaa ctg att gat tat cat gtc gcc agc ggt act tcg gcg atc          388
Leu Lys Lys Leu Ile Asp Tyr His Val Ala Ser Gly Thr Ser Ala Ile
     25                  30                  35 gtt tct gtt ggc acc act ggc gag tcc gct acc tta aat cat gac gaa          436
Val Ser Val Gly Thr Thr Gly Glu Ser Ala Thr Leu Asn His Asp Glu
 40                  45                  50                  55 cat gct gat gtg gtg atg atg acg ctg gat ctg gct gat ggg cgc att          484
His Ala Asp Val Val Met Met Thr Leu Asp Leu Ala Asp Gly Arg Ile
```

```
                          60                  65                  70
ccg gta att gcc ggg acc ggc gct aac gct act gcg gaa gcc att agc       532
Pro Val Ile Ala Gly Thr Gly Ala Asn Ala Thr Ala Glu Ala Ile Ser
                75                  80                  85 ctg acg cag cgc ttc aat gac agt ggt atc gtc ggc tgc ctg acg gta       580
Leu Thr Gln Arg Phe Asn Asp Ser Gly Ile Val Gly Cys Leu Thr Val
        90                  95                 100 acc cct tac tac aat cgt ccg tcg caa gaa ggt ttg tat cag cat ttc       628
Thr Pro Tyr Tyr Asn Arg Pro Ser Gln Glu Gly Leu Tyr Gln His Phe
    105                 110                 115 aaa gcc atc gct gag cat act gac ctg ccg caa att ctg tat aat gtg       676
Lys Ala Ile Ala Glu His Thr Asp Leu Pro Gln Ile Leu Tyr Asn Val
120                 125                 130                 135 ccg tcc cgt act ggc tgc gat ctg ctc ccg gaa acg gtg ggc cgt ctg       724
Pro Ser Arg Thr Gly Cys Asp Leu Leu Pro Glu Thr Val Gly Arg Leu
                140                 145                 150 gcg aaa gta aaa aat att atc gga atc aaa gag gca aca ggg aac tta       772
Ala Lys Val Lys Asn Ile Ile Gly Ile Lys Glu Ala Thr Gly Asn Leu
            155                 160                 165 acg cgt gta aac cag atc aaa gag ctg gtt tca gat gat ttt gtt ctg       820
Thr Arg Val Asn Gln Ile Lys Glu Leu Val Ser Asp Asp Phe Val Leu
        170                 175                 180 ctg agc ggc gat gat gcg agc gcg ctg gac ttc atg caa ttg ggc ggt       868
Leu Ser Gly Asp Asp Ala Ser Ala Leu Asp Phe Met Gln Leu Gly Gly
    185                 190                 195 cat ggg gtt att tcc gtt acg act aac gtc gca gcg cgt gat atg gcc       916
His Gly Val Ile Ser Val Thr Thr Asn Val Ala Ala Arg Asp Met Ala
200                 205                 210                 215 cag atg tgc aaa ctg gca gca gaa gaa cat ttt gcc gag gca cgc gtt       964
Gln Met Cys Lys Leu Ala Ala Glu Glu His Phe Ala Glu Ala Arg Val
                220                 225                 230 att aat cag cgt ctg atg cca tta cac aac aaa cta ttt gtc gaa ccc      1012
Ile Asn Gln Arg Leu Met Pro Leu His Asn Lys Leu Phe Val Glu Pro
            235                 240                 245 aat cca atc ccg gtg aaa tgg gca tgt aag gaa ctg ggt ctt gtg gcg      1060
Asn Pro Ile Pro Val Lys Trp Ala Cys Lys Glu Leu Gly Leu Val Ala
        250                 255                 260 acc gat acg ctg cgc ctg cca atg aca cca atc acc gac agt ggt cgt      1108
Thr Asp Thr Leu Arg Leu Pro Met Thr Pro Ile Thr Asp Ser Gly Arg
    265                 270                 275 gag acg gtc aga gcg gcg ctt aag cat gcc ggt ttg ctg taa              1150
Glu Thr Val Arg Ala Ala Leu Lys His Ala Gly Leu Leu
280                 285                 290 agtttaggga gatttgatgg cttactctgt tcaaaagtcg cgcctgg                  1197

<210> SEQ ID NO 14
<211> LENGTH: 292
<212> TYPE: PRT
<213> ORGANISM: Escherichia coli

<400> SEQUENCE: 14

Met Phe Thr Gly Ser Ile Val Ala Ile Val Thr Pro Met Asp Glu Lys
 1               5                  10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60
```

```
Asp Leu Ala Asp Gly Arg Ile Pro Val Ile Ala Gly Thr Gly Ala Asn
 65                  70                  75                  80

Ala Thr Ala Glu Ala Ile Ser Leu Thr Gln Arg Phe Asn Asp Ser Gly
                 85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290
```

METHOD FOR PRODUCING L-AMINO ACID USING METHYLOTROPH

This application claims priority under 35 U.S.C. §119 to Japanese Patent Application No. 2002-336346, filed Nov. 20, 2002.

BACKGROUND OF THE INVENTION

1. Technical Field of the Invention

The present invention relates to a method for producing an L-amino acid, and a bacterium used therefor. More precisely, the present invention relates to a methane-utilizing bacterium having improved L-amino acid producing ability and a method for producing an L-amino acid utilizing the bacterium.

2. Description of the Related Art

Conventionally, L-amino acids such as L-lysine, L-glutamic acid, L-threonine, L-leucine, L-isoleucine, L-valine and L-phenylalanine are produced by fermentation utilizing coryneform bacteria belonging to the genus *Brevibacterium*, *Corynebacterium* or *Microbacterium* (Amino Acid Fermentation, the Japan Scientific Societies Press [Gakkai Shuppan Center], pp. 195–215, 1986). Furthermore, microorganisms of the genus *Bacillus, Streptomyces, Penicillium* (U.S. Pat. No. 3,220,929), *Pseudomonas, Arthrobacter, Serratia, Aerobacter, Candida* (U.S. Pat. No. 3,563,857), *Escherichia* (Japanese Patent Laid-open (Kokai) No. 5-244970) and the like can also be utilized in the production of L-amino acids.

To improve productivity of these microorganisms, bacterial strains isolated from nature, or artificial mutants of the bacterial strains, have been used. Furthermore, various techniques have been disclosed for increasing L-amino acid producing ability by enhancing L-amino acid biosynthesis enzymes using recombinant DNA techniques (U.S. Pat. Nos. 4,278,765, 4,346,170 and 6,040,160).

Methanol is a raw material often used in fermentation which is inexpensive and widely and easily available. Methods for producing L-amino acids by fermentation of methanol have been known using microorganisms that belong to the genus *Achromobacter* or *Pseudomonas* (Japanese Patent Publication (Kokoku) No. 45-25273), *Protaminobacter* (Japanese Patent Laid-open Publication (Kokai) No. 49-125590), *Protaminobacter* or *Methanomonas* (Japanese Patent Laid-open (Kokai) No. 50-25790), *Microcyclus* (Japanese Patent Laid-open (Kokai) No. 52-18886), *Methylobacillus* (Japanese Patent Laid-open (Kokai) No. 4-91793), *Bacillus* (Japanese translation of PCT international application Patent (Kohyo) No. 3-505284 (WO90/12105)) and the like. The inventors of the present invention to date have developed methods for producing L-amino acids using *Methylophilus* bacteria employing breeding techniques utilizing artificial mutagenesis and recombinant DNA (WO00/61723).

Techniques are also known for enhancing L-amino acid producing ability by introducing genes coding for glycolytic enzymes such as glucose-6-phosphate isomerase (International Patent Publication No. 01/02542 (WO 01/02542 A1)), fructose phosphotransferase (International Patent Publication No. 01/48146 (WO 01/48146 A1)) and enolase (International Patent Publication No. 01/02543 (WO 01/02543 A1)).

Many methanol-utilizing bacteria including enterobacteria have the Entner-Doudoroff pathway as one of their methanol metabolic pathways. This pathway involves 6-phosphogluconate dehydratase (abbreviated as "EDD" hereinafter), which catalyzes a reaction to produce 2-keto-3-deoxy-6-phosphogluconate from 6-phosphogluconic acid, and 2-keto-3-deoxy-6-phosphogluconate aldolase (abbreviated as "EDA" hereinafter), which cleaves 2-keto-3-deoxy-6-phosphogluconate to produce glyceraldehyde-3-phosphate and pyruvic acid. Genes coding for EDD and EDA have been cloned from *Escherichia coli, Zymomonas mobilis* and so forth, and their nucleotide sequences have been reported (Mol. Microbiol. 5, 2901–2911; J. Bacteriol. 172 (12), 7227–7240 (1990)). The nucleotide sequences of the gene coding for EDD (edd) and the gene coding for EDA (eda) of *Escherichia coli* are registered as GenBank accession number L20897. Furthermore, the nucleotide sequence of the eda gene of *Zymomonas mobilis* is registered as GenBank accession number X58364, and the nucleotide sequence of the edd gene is registered as GenBank accession number M60615 M37982 in the database.

There is clearly a need in the art for efficient, low-cost, productive methods of obtaining amino acids for both agricultural and nutritional uses. The relationship between the Entner-Doudoroff pathway and the productivity of L-amino acids has not previously been described. The present invention describes this relationship and a method of exploiting it.

SUMMARY OF THE INVENTION

An object of the present invention is to fulfill this need in the art and provide a method for improving productivity of L-amino acids in bacteria using a unique and novel approach.

It is an object of the present invention to provide a method for producing an L-amino acid comprising culturing a microorganism having an ability to produce an L-amino acid in a medium, whereby said L-amino acid accumulates in the medium, and collecting said L-amino acid from the medium, wherein said microorganism is a methanol-utilizing bacterium having the Entner-Doudoroff pathway and modified so that 6-phosphogluconate dehydratase activity and/or 2-keto-3-deoxy-6-phosphogluconate aldolase activity are enhanced, and said L-amino acid is selected from L-amino acids produced by a biosynthetic pathway which utilizes pyruvic acid as an intermediate.

It is a further object of the present invention to provide the method as described above, wherein the methanol-utilizing bacterium comprises a bacterium belonging to the genus *Methylophilus*.

It is a further object of the present invention to provide the method as described above, wherein said 6-phosphogluconate dehydratase activity and/or 2-keto-3-deoxy-6-phosphogluconate aldolase activity is enhanced by increasing the copy number of a gene coding for 6-phosphogluconate dehydratase and/or 2-keto-3-deoxy-6-phosphogluconate aldolase, or modifying an expression regulatory sequence of the gene so that expression of the gene should be enhanced in a cell of the bacterium.

It is a further object of the present invention to provide the method as described above, wherein said L-amino acid is selected from L-lysine, L-leucine, L-isoleucine and L-valine.

It is a further object of the present invention to provide a methanol-utilizing bacterium having the Entner-Doudoroff pathway, whereby said bacterium is modified so that 6-phosphogluconate dehydratase activity and/or 2-keto-3-deoxy-6-phosphogluconate aldolase activity is enhanced, and has an ability to produce an L-amino acid via a biosynthetic pathway which utilizes pyruvic acid as an intermediate.

According to the present invention, an L-amino acid producing ability of a microorganism having the Entner-Doudoroff pathway is described herein.

DESCRIPTION OF THE PREFERRED EMBODIMENTS

Figure 1:
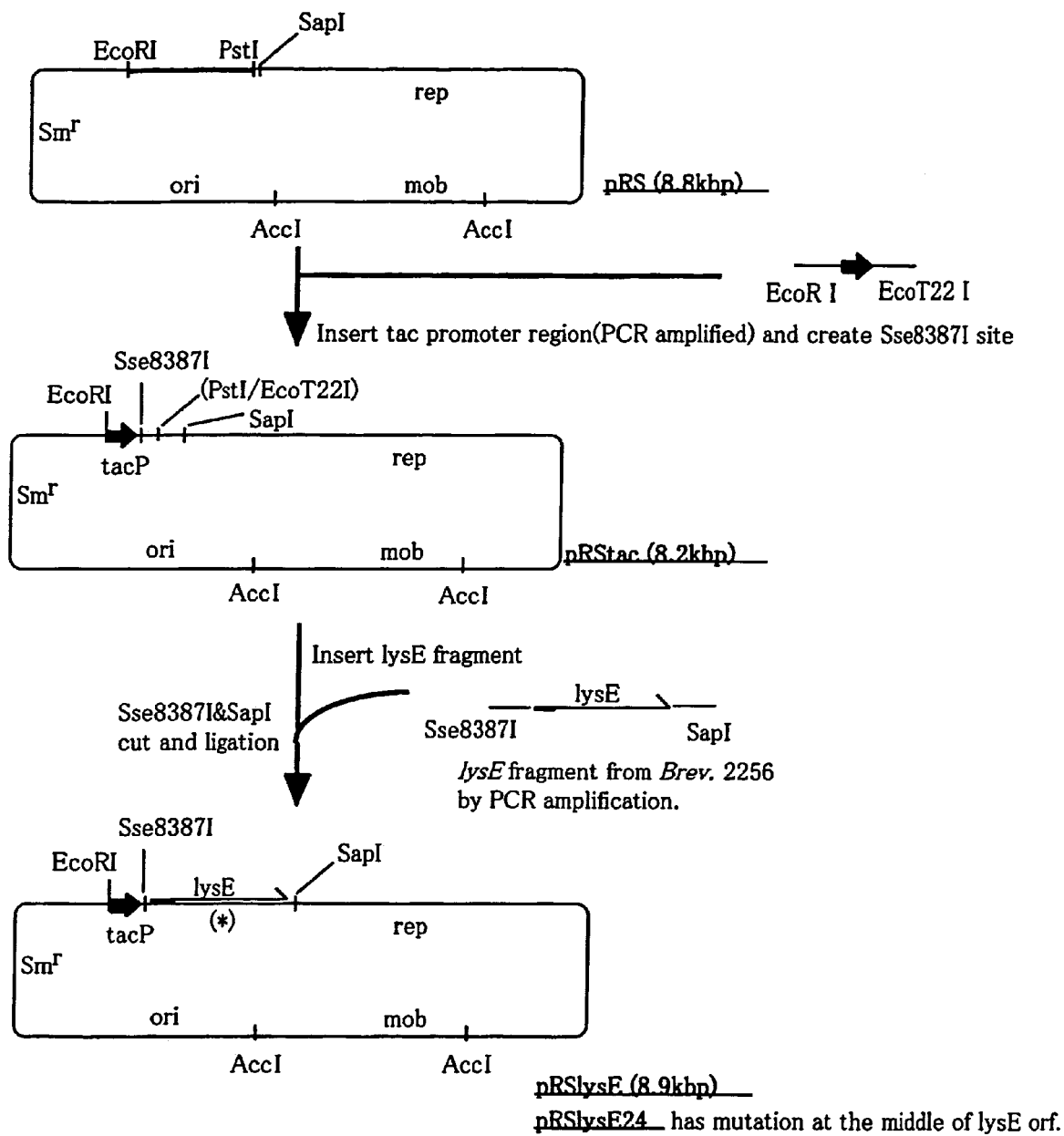
FIG. 1 shows constructions of a plasmid pRStac having the tac promoter and plasmids pRSlysE and pRSlysE24 consisting of the plasmid pRStac inserted with the lysE gene or lysE24 gene.

The inventors of the present invention focused their attention on the Entner-Doudoroff pathway (hereinafter "ED pathway") among the metabolic pathways for synthesis of pyruvic acid from sugar phosphate compounds. The major metabolic pathways from methanol to pyruvic acid, which serves as a starting material for synthesis of L-amino acids such as L-lysine in Gram-negative strict methanol-utilizing bacteria are considered to be the Embden-Meyerhof-Parnas pathway (henceforth also referred to as "EMP pathway") and the Entner-Doudoroff pathway.

The inventors of the present invention first enhanced enzymatic activities of phosphofructokinase, phosphoglycerate kinase etc. in order to increase supply of pyruvic acid. However, when enhancement of the enzymatic activity was attempted, the genes of the corresponding enzymes could not be introduced into cells of the target methanol-utilizing bacteria, or the production amount of the final product, L-lysine, was not affected, even if they were introduced. Therefore, research was performed in order to enhance the flow of the metabolites involved in the ED pathway.

Two of methods were considered to increase the supply of pyruvic acid utilizing the ED pathway, i.e., (1) eliminating or attenuating genes of glucose-6-phosphate dehydrogenase etc., and (2) enhancing the Entner-Doudoroff pathway. Although both of the methods can similarly be expected to provide improvement in the amount of pyruvic acid, method (2) focuses on the metabolism of the pyruvic acid and ribulose monophosphate pathways, and how they could be balanced by controlling degrees of activities. It is also possible to supply ribulose-5-phosphate, which is an intermediate of the ribulose monophosphate pathway, and nucleic acids, which are derivatives of the intermediates. As a result of this research, it was found that an L-amino acid producing ability of methanol-utilizing bacteria could be improved by enhancing the Entner-Doudoroff pathway, and thus accomplished the present invention.

<1> Bacterium of the Present Invention

The methanol-utilizing bacterium used for the present invention is a methanol-utilizing bacterium having an ability to produce an L-amino acid and the Entner-Doudoroff pathway.

The term "an ability to produce an L-amino acid" used in the present invention means an ability to cause accumulation of the L-amino acid in a medium when the bacterium of the present invention is cultured in the medium. This ability to produce an L-amino acid may be a property of a wild-type strain of the methanol-utilizing bacterium, or a property imparted or enhanced by breeding. L-amino acids to which the present invention can be applied are L-amino acids produced by a biosynthetic pathway utilizing pyruvic acid as an intermediate. Specific examples include L-lysine, L-glutamic acid, L-threonine, L-leucine, L-isoleucine, L-valine, L-serine, L-alanine, L-tyrosine, L-phenylalanine and so forth.

As shown in the examples section, a bacterium having the Entner-Doudoroff pathway enhanced by increasing activities of EDD and EDA showed increased production of L-valine. Since L-valine is produced from pyruvic acid, increase in production of L-valine indicates an increase in the amount of supplied pyruvic acid. Therefore, the bacterium having the enhanced Entner-Doudoroff pathway is expected to have an increased ability to produce any L-amino acid produced by a biosynthetic pathway utilizing pyruvic acid as an intermediate.

Specific examples of the methanol-utilizing bacteria having the Entner-Doudoroff pathway include bacteria belonging to the genera *Methylophilus*, *Methylobacillus* and so forth. Whether a bacterium has the Entner-Doudoroff pathway or not can be determined by, for example, mixing a cell-disrupted suspension with glyceraldehyde-3-phosphate dehydrogenase, 6-phosphogluconic acid and acetylpyridine adenine dinucleotide and detecting glyceraldehyde-3-phosphate produced from 6-phosphogluconic acid as a substrate by measuring increase of absorbance at 365 nm. A bacterium that is known to produce glyceraldehyde-3-phosphate has the Entner-Doudoroff pathway.

In the present invention, the methanol-utilizing bacterium, that is, methylotroph, means a bacterium which can grow by consuming methanol as a major carbon source, and in which an ability to produce an L-amino acid is enhanced or imparted by being modified to enhance EDD and/or EDA activity. Specific examples include *Methylophilus* bacteria such as *Methylophilus methylotrophus* and *Methylobacillus* bacteria such as *Methylobacillus* glycogenes and *Methylobacillus flagellatum*.

Specific examples of *Methylophilus* bacteria include the *Methylophilus methylotrophus* AS1 strain (NCIMB10515) and so forth. The *Methylophilus methylotrophus* AS1 strain (NCIMB10515) is available form the National Collections of Industrial and Marine Bacteria (Address: NCIMB Lts., Torry Research Station, 135, Abbey Road, Aberdeen AB9 8DG, United Kingdom).

Furthermore, examples of *Methylobacillus* glycogenes include the T-11 strain (NCIMB 11375), ATCC 21276 strain, ATCC 21371 strain, ATR80 strain (described in Appl. Microbiol. Biotechnol., 42, pp. 67–72 (1994)), A513 strain (described in Appl. Microbiol. Biotechnol., 42, pp. 67–72 (1994)) and so forth. The *Methylobacillus* glycogenes NCIMB 11375 strain is available from the National Collections of Industrial and Marine Bacteria (Address: NCIMB Lts., Torry Research Station, 135, Abbey Road, Aberdeen AB9 8DG, United Kingdom). Examples of *Methylobacillus flagellatum* include the KT strain (described in Arch. Microbiol., 149, pp. 441–446 (1988)) and so forth.

The methanol-utilizing bacterium of the present invention is a bacterium which has an ability to produce an L-amino acid and the aforementioned Entner-Doudoroff pathway, and which has been modified so that the EDD and/or EDA activity is enhanced. The bacterium of the present invention is preferably a methanol-utilizing bacterium which has been modified so that the activities of both EDD and EDA are enhanced.

The expression "modified so that EDD or EDA activity is enhanced" means that EDD or EDA activity per cell is made higher than that of a wild-type methanol-utilizing bacterium. For example, those in which the number of EDD or EDA molecules per cell is increased, those in which specific activity of EDD or EDA per EDD or EDA molecule is increased and so forth are encompassed. Furthermore, the wild-type methanol-utilizing bacterium should be compared to a methanol-utilizing bacterium that has not been subjected to any manipulation for enhancing EDD or EDA activity.

Enhancement of the EDD and/or EDA activity in a bacterium can be achieved by increasing copy number of a gene coding for EDD and/or EDA. For example, recombinant DNA can be prepared by ligating a gene fragment coding for EDD and/or EDA with a vector functioning in a target bacterium, preferably a multi-copy type vector, and can be introduced into the bacterium to transform it. When both of activities of EDD and EDA are to be enhanced, the gene fragment coding for EDD and the gene fragment coding for EDA may be separately incorporated into different vectors, but they are preferably incorporated into the same vector. The recombinant DNA may be introduced into a bacterium having an L-amino acid producing ability, alternatively the recombinant DNA may be introduced into a wild-type bacterium to obtain a transformant strain, and then the transformant strain may be imparted with the L-amino acid producing ability.

Any of the genes derived from bacteria having the Entner-Doudoroff pathway can be used as the gene coding for EDD and the gene coding for EDA. Specifically, genes derived from *Escherichia* bacteria are encompassed by the present invention. It has been reported that the gene coding for EDD (edd) and gene coding for EDA (eda) derived from *Escherichia coli* form an operon (J. Bacteriol., 174 (14): 4638–46, July 1992). Hereinafter, the gene coding for EDD is referred to as edd, and the gene coding for EDA is referred to as eda. Furthermore, such genes of bacteria of the genus *Zymomonas* have also been reported, and the edd gene and eda gene can be obtained by PCR (Polymerase Chain Reaction, see White, T. J. et al., Trends Genet. 5, 185 (1989)) using primers prepared based on the sequences of those genes, or hybridization using a probe prepared based on the aforementioned gene sequences. For example, an operon fragment containing the edd and eda genes of *Escherichia coli* can be obtained by PCR using primers edd-F (SEQ ID NO: 11) and eda-R (SEQ ID NO: 12). The edd gene and eda gene of other microorganisms can be similarly obtained. The hybridization condition is exemplified by a condition under which washing is performed at a salt concentration corresponding to 1×SSC, 0.1% SDS, preferably 0.1×SSC, 0.1% SDS, at 60° C.

Furthermore, the edd gene and eda gene used are not limited to wild-type genes, but the present invention also encompasses mutants or artificially modified genes coding for gene products, including substitution, deletion, insertion, addition or the like of one or several amino acids at one or more sites, so long as the functions of the encoded EDD and EDA are not diminished. Although the number of "several" amino acids referred to herein differs depending on the position or type of amino acid residues in a three-dimensional structure of a protein, but it may be specifically 2 to 60, preferably, 2 to 40, more preferably 2 to 20. Furthermore, as DNA coding for a protein substantially identical to the aforementioned EDD and/or EDA, the present invention encompasses DNA hybridizable with nucleotide sequences of a known edd or eda gene (for example, GenBank accession L20897, X58364, M60615, M37982) or a probe that can be produced from these nucleotide sequences under stringent conditions and codes for a protein having an activity similar to that of EDD or EDA. "Stringent conditions" means conditions under which a so-called specific hybrid is formed, and a non-specific hybrid is not formed. It is difficult to clearly express this condition by using numerical values. However, for example, the stringent condition includes a condition under which DNAs having high homology, for example, DNAs having homology of 70% or more, preferably 80% or more, more preferably 90% or more, most preferably 95% more, are hybridized with each other, but DNAs having homology lower than the above are not hybridized with each other. Alternatively, stringent conditions are exemplified by conditions under which DNAs are hybridized with each other at a salt concentration corresponding to typical washing conditions of Southern hybridization, i.e., 1×SSC, 0.1% SDS, preferably 0.1×SSC, 0.1% SDS, at 60° C.

Chromosomal DNA can be prepared from a bacterium as a DNA donor by, for example, the method of Saito and Miura (refer to H. Saito and K. Miura, Biochem. Biophys. Acta, 72, 619 (1963); Text for Bioengineering Experiments, Edited by the Society for Bioscience and Bioengineering, Japan, pp. 97–98, Baifukan, 1992) and the like.

If a recombinant DNA is prepared by ligating the edd and/or eda genes amplified by PCR with vector DNA autonomously replicable in a cell of *Escherichia coli* or the like and introduced into *Escherichia coli*, subsequent operations become easier. Examples of the vector autonomously replicable in the *Escherichia coli* cell include pMW219, pSTV28, pUC19, pUC18, pHSG299, pHSG399, pHSG398, RSF1010, pBR322, pACYC184 and so forth.

In order to introduce a recombinant DNA prepared as described above into a *Methylophilus* bacterium, any method can be used so long as it provides sufficient transformation efficiency. For example, electroporation can be used (Canadian Journal of Microbiology, 43, 197 (1997)).

The copy number of the edd and/or eda gene can also be increased by allowing multiple copies of these genes to exist in chromosomal DNA of a bacterium. To introduce multiple copies of the edd and/or eda gene into chromosomal DNA of a bacterium, homologous recombination is carried out by using a sequence whose multiple copies exist in the chromosomal DNA as a target. As sequences whose multiple copies exist in the chromosomal DNA, repetitive DNA or inverted repeat existing at an end of transposable element can be used. Furthermore, as disclosed in Japanese Patent Laid-open No. 2-109985, it is also possible to incorporate the edd and/or eda gene into a transposon, and allow it to be transferred to introduce multiple copies of the genes into the chromosomal DNA.

Besides the aforementioned gene amplification methods, the enhancement of EDD and/or EDA activities can also be attained by replacing an expression regulatory sequence such as a promoter of the edd and/or eda gene in chromosomal DNA or plasmid with a stronger one. For example, lac promoter, trp promoter, trc promoter and so forth are known as strong promoters. Furthermore, as disclosed in International Patent Publication WO00/18935, by introducing a substitution of several nucleotides into the promoter region of the edd and/or eda gene, the promoter can be modified so to become stronger. Substitution or modification of these promoters enhances expression of the edd and/or eda gene, and thus activities of EDD and/or EDA are enhanced. Modification of these expression regulatory sequences can be combined with the increase in copy number of the edd and/or eda gene.

Enhancement of the activities of EDD and EDA can be confirmed by mixing a cell-disrupted suspension with glyceraldehyde-3-phosphate dehydrogenase and 6-phosphogluconic acid and measuring glyceraldehyde-3-phosphate produced from 6-phosphogluconic acid as a substrate. In this reaction, EDD activity can be measured by quantifying 6-phosphogluconic acid remaining after the reaction by using 6-phosphogluconate dehydrogenase, or quantifying pyruvic acid produced in the presence of excessive 2-keto-3-deoxy-6-phosphogluconate aldolase using lactate dehydrogenase. The 6-phosphogluconic acid or pyruvic acid can be quantified as increase of NADH in the dehydrogenase reaction. Furthermore, the EDA activity can also be measured by detecting pyruvic acid produced from 2-keto-3-deoxy-6-phosphogluconate as a substrate by using lactate dehydrogenase.

<2> Methanol-Utilizing Bacterium of the Present Invention

The bacterium of the present invention is a methanol-utilizing bacterium which is modified so that the EDD and/or EDA activity are enhanced, and has an ability to produce an L-amino acid via a biosynthesis pathway where pyruvic acid is an intermediate. Examples of L-amino acids encompassed include L-lysine, L-glutamic acid, L-threonine, L-leucine, L-isoleucine, L-valine, L-serine, L-alanine, L-tyrosine, L-phenylalanine and so forth.

The bacterium of the present invention can be obtained by modifying a methanol-utilizing bacterium having an ability to produce an L-amino acid so that the EDD and/or EDA activity is enhanced. The methanol-utilizing bacterium of the present invention can also be obtained by imparting an ability to produce an L-amino acid to a methanol-assimilating bacterium modified so that the EDD and/or EDA activity are enhanced. Furthermore, the methanol-utilizing bacterium of the present invention may be a bacterium imparted with an ability to produce an L-amino acid due to such modification that the EDD and/or EDA activity should be enhanced.

A methanol-utilizing bacterium having an ability to produce an L-amino acid can be obtained by imparting an ability to produce an L-amino acid to a wild-type strain of a methanol-utilizing bacterium. In order to impart an ability to produce an L-amino acid, methods conventionally used for breeding of coryneform bacteria, *Escherichia* bacteria and so forth, can be used, for example, acquisition of auxotrophic mutant strains, analogue resistant strains or metabolic regulation mutant strains, creation of recombinant strains in which an L-amino acid biosynthesis system enzyme is enhanced (refer to "Amino Acid Fermentation", the Japan Scientific Societies Press [Gakkai Shuppan Center], 1st Edition, published on May 30, 1986, pp. 77–100) and so forth. When breeding of L-amino acid producing bacteria, properties of auxotrophy, analogue resistance, metabolic regulation mutation and so forth may be individually imparted or two or more of them may be imparted in combination. The biosynthesis system enzymes may be individually enhanced or two or more of them may be enhanced in combination. Furthermore, imparting properties including auxotrophy, analogue resistance, metabolic regulation mutation and so forth may be combined with the enhancement of biosynthesis system enzyme.

For example, L-lysine producing bacteria can be bred as mutant strains exhibiting auxotrophy for L-homoserine or L-threonine and L-methionine (Japanese Patent Publication Nos. 48-28078 and 56-6499), mutant strains exhibiting auxotrophy for inositol or acetic acid (Japanese Patent Laid-open Nos. 55-9784 and 56-8692), or mutant strains that are resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine.

Hereinafter, a method for imparting or enhancing an ability to produce an L-amino acid by enhancing the expression of a gene for an enzyme in an L-amino acid biosynthesis system will be described.

L-lysine producing ability can be imparted by, for example, enhancing activities of dihydrodipicolinate synthase and aspartokinase.

Activities of dihydrodipicolinate synthase and aspartokinase in a methanol-utilizing bacterium can be enhanced by transforming the methanol-utilizing bacterium host with a recombinant DNA prepared by ligating a gene fragment encoding dihydrodipicolinate synthase and a gene fragment encoding aspartokinase with a vector that functions in the methanol-utilizing bacterium, preferably a multiple copy type vector. As a result of the increase in the copy number of the gene encoding dihydrodipicolinate synthase and the gene encoding aspartokinase in cells of the transformant strain, activities of these enzymes can be enhanced. Hereafter, dihydrodipicolinate synthase, aspartokinase and aspartokinase III are also referred to with abbreviations of DDPS, AK and AKIII, respectively.

Any microorganisms can be used as a microorganism providing a gene that encodes DDPS and a gene that encodes AK, so long as the microorganism can express DDPS activity and AK activity in a methanol-utilizing bacterium. Such microorganisms may be wild-type strains or mutant strains derived therefrom. Specifically, examples of such microorganisms include *E. coli* (*Escherichia coli*) K-12 strain and *Methylophilus methylotrophus* AS1 strain (NCIMB10515) and so forth. Since nucleotide sequences are known for the gene encoding DDPS derived from *Escherichia* bacteria (dapA, Richaud, F. et al., J. Bacteriol., 297 (1986)) and the gene encoding AKIII derived from *Escherichia* bacteria (lysC, Cassan, M., Parsot, C., Cohen, G. N. and Patte, J. C., J. Biol. Chem., 261, 1052 (1986)), these genes can be obtained by PCR using primers synthesized based on the nucleotide sequences of these genes and chromosomal DNA of microorganism such as *E. coli* K-12 as a template. As specific examples, dapA and lysC derived from *E. coli* will be explained below. However, genes used for the present invention are not limited to them.

In the present invention, it is preferred that DDPS and AK are not subject to feedback inhibition by L-lysine. It is known that wild-type DDPS derived from *E. coli* is subject to feedback inhibition by L-lysine, and that wild-type AKIII derived from *E. coli* is subject to suppression and feedback inhibition by L-lysine. Therefore, dapA and lysC which are introduced into a methanol-utilizing bacterium preferably encode DDPS and AKIII having a mutation that eliminates the feedback inhibition by L-lysine, respectively. Hereinafter, DDPS having a mutation that eliminates the feedback inhibition by L-lysine may also be referred to as "mutant DDPS", and a DNA encoding the mutant DDPS may also be referred to as "mutant dapA or dapA*". AKIII derived from *E. coli* having a mutation that eliminates the feedback inhibition by L-lysine may also be referred to as "mutant AKIII", and a DNA encoding the mutant AKIII may also be referred to as "mutant lysC".

In the present invention, DDPS and AK are not necessarily required to be mutated. It has been known that, for example, wild-type DDPS derived from *Corynebacterium* bacteria does not suffer feedback inhibition by L-lysine.

A nucleotide sequence of wild-type dapA derived from *E. coli* is exemplified in SEQ ID NO: 13, and the amino acid sequence of wild-type DDPS encoded by the nucleotide sequence is exemplified in SEQ ID NO: 14.

The DNA encoding mutant DDPS that is not subject to feedback inhibition by L-lysine may be a DNA encoding DDPS having the amino acid sequence of SEQ ID NO: 14, but whereby the histidine residue at position 118 is substituted with a tyrosine residue. Furthermore, the DNA encoding mutant AKIII that is not subject to feedback inhibition by L-lysine may be a DNA encoding AKIII whereby the threonine residue at position 352 is substituted with an isoleucine residue (U.S. Pat. No. 6,040,160).

The plasmid used for gene cloning may be any plasmid so long as it can replicate in microorganisms such as *Escherichia* bacteria, and includes, but is not limited to pBR322, pTWV228, pMW119, pUC19 and so forth.

The vector that functions in methanol-utilizing bacteria is exemplified by, for example, a plasmid that can autonomously replicate in methanol-utilizing bacteria. Specifically, RSF1010, which is a broad host spectrum vector, and derivatives thereof, for example, pAYC32 (Chistorerdov, A. Y., Tsygankov, Y. D. Plasmid, 16, 161–167 (1986)), pMFY42 (Gene, 44, 53 (1990)), pRP301, pTB70 (Nature, 287, 396, (1980)) and so forth are encompassed.

To prepare a recombinant DNA by ligating dapA and lysC to a vector that functions in a methanol-utilizing bacterium, the vector is digested with a restriction enzyme suitable for the ends of a DNA fragment containing dapA and lysC. The ligation is usually performed by using a ligase such as T4 DNA ligase. dapA and lysC may be incorporated into separate vectors or the same vector.

A broad host spectrum plasmid RSFD80 (WO95/16042) can be used as a plasmid having a mutant dapA coding for a mutant DDPS and a mutant lysC coding for a mutant AKIII. The *E. coli* JM109 strain transformed with this plasmid was designated as AJ12396, which was deposited at National Institute of Bioscience of Advanced Industrial Science and Technology on Oct. 28, 1993 and received an accession number of FERM P-13936. Then, the deposit was converted to an international deposit under the provisions of the Budapest Treaty on Nov. 1, 1994 and received an accession number of FERM BP-4859. RSFD80 can be obtained from the AJ12396 strain using known methods.

The mutant dapA contained in RSFD80 has a sequence consisting of a nucleotide sequence of wild-type dapA shown in SEQ ID NO: 13 in which C of the nucleotide number 623 is changed to T. As a result, the encoded mutant DDPS has an amino acid sequence of SEQ ID NO: 14, except the histidine residue at position 118 is changed to a tyrosine residue. Furthermore, the mutant lysC contained in RSFD80 has a nucleotide sequence of wild-type lysC in which the nucleotide residue C at position 1638 is changed to T (U.S. Pat. No. 6,040,160). As a result, the encoded mutant AKIII has a sequence where the threonine residue at position 352 is substituted with an isoleucine residue.

Any method can be used to introduce a recombinant DNA prepared as described above into a methanol-utilizing bacterium, so long as it provides sufficient transformation efficiency. For example, electroporation can be used (Canadian Journal of Microbiology, 43, 197 (1997)).

The DDPS activity and AK activity can also be enhanced by allowing multiple copies of dapA and lysC to exist on chromosomal DNA of a methanol-utilizing bacterium. In order to introduce multiple copies of dapA and lysC into chromosomal DNA of a methanol-utilizing bacterium, homologous recombination is performed by using a sequence that is present on chromosomal DNA in a multiple copy number as a target. A repetitive DNA or an inverted repeat present at the end of a transposable element can be used as a sequence present on chromosomal DNA in a multiple copy number. Alternatively, as disclosed in Japanese Patent Laid-open (Kokai) No. 2-109985, multiple copies of dapA and/or lysC can be introduced into chromosomal DNA by incorporating them into a transposon and transferring it. In both of the methods, as a result of increased copy numbers of dapA and lysC in transformant strains, activities of DDPS and AK are amplified.

Besides the above gene amplification, the desired gene can be enhanced by replacing an expression control sequence such as promoters of dapA and lysC with stronger ones (refer to Japanese Patent Laid-open No. 1-215280). As such strong promoters, there are known, for example, lac promoter, trp promoter, trc promoter, tac promoter, PR promoter and PL promoter of lambda phage, tet promoter, amyE promoter, spac promoter and so forth. Substitution of these promoters enhances expression of the desired gene, and thus the activity of the enzyme encoded by desired gene is amplified. Enhancement of expression control sequence can be combined with increase of the copy number of desired gene.

In order to prepare a recombinant DNA by ligating a gene fragment and a vector, the vector is digested with a restriction enzyme corresponding to the terminus of the gene fragment. Ligation is usually performed by ligase such as T4 DNA ligase. As methods for digestion, ligation and others of DNA, preparation of chromosomal DNA, PCR, preparation of plasmid DNA, transformation, design of oligonucleotides used as primers and so forth, usual methods well known to those skilled in the art can be used. Such methods are described in Sambrook, J., Fritsch, E. F., and Maniatis, T., "Molecular Cloning A Laboratory Manual, Second Edition", Cold Spring Harbor Laboratory Press (1989) and so forth.

In addition to the enhancement of DDPS and AK, other enzymes involved in the L-lysine biosynthesis may also be enhanced. Such enzymes include diaminopimelate pathway enzymes such as dihydrodipicolinate reductase, diaminopimelate decarboxylase, diaminopimelate dehydrogenase (refer to WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase and aspartate semialdehyde dehydrogenase, aminoadipate pathway enzymes such as homoaconitate hydratase and so forth.

Aspartokinase, aspartate semialdehyde dehydrogenase, dihydrodipicolinate synthase, dihydrodipicolinate reductase and diaminopimelate decarboxylase derived from *Methylophilus methylotrophus* as a methanol-utilizing bacterium, are described in WO 00/61723.

Furthermore, the microorganisms of the present invention may have decreased activity of an enzyme that catalyzes a reaction for generating a compound other than L-lysine by branching off from the biosynthetic pathway for L-lysine, or may be deficient in such an enzyme. Illustrative examples of the enzyme that catalyzes a reaction for generating a compound other than L-lysine by branching off from the biosynthetic pathway for L-lysine include homoserine dehydrogenase (see WO95/23864).

The aforementioned techniques for enhancing activities of enzymes involved in the L-lysine biosynthesis can be similarly used for other L-amino acids. The methanol-utilizing bacterium of the present invention may have wild-type phenotype, except for being modified so that the EDD and/or EDA activity is enhanced, so long as it has an ability to produce an L-amino acid.

Furthermore, an ability to produce an L-amino acid can also be improved by enhancing an activity of protein involved in extracellular secretion of the L-amino acid. For example, as a protein involved in extracellular secretion of L-lysine, the LysE protein encoded by the lysE gene is known. The inventors of the present invention confirmed that, although a wild-type lysE derived form *Brevibacterium* bacteria did not function at all in *Methylophilus* bacteria or *Methylobacillus* bacteria, it can be modified so as to function in a methylotroph. Examples of such variants of the LysE protein include LysE24, and are described in the examples section.

The LysE protein that is encoded by the lysE gene has six hydrophobic helix regions. Some of these hydrophobic regions are thought to be transmembrane domains. It is also thought that a region between the third and fourth regions from the N-terminus is hydrophilic and has a loop structure. In the present invention, this hydrophilic region is called a loop region. The nucleotide sequence of wild-type lysE and the amino acid sequence of the LysE protein of *Brevibacterium lactofermentum* are shown in SEQ ID NOS: 7 and 8. In this amino acid sequence, hydrophobic helix regions correspond to the amino acid numbers 5 to 20, 37 to 58, 67 to 93, 146 to 168, 181 to 203 and 211 to 232. The loop region corresponds to the amino acid numbers 94 to 145.

The inventors of the present invention found that the lysE gene was lethal when expressed in a methanol-utilizing bacterium, but DNA encoding a variant of the LysE protein missing the loop region, or substantially consisted only of the hydrophobic helixes, promoted the secretion of L-lysine and/or L-arginine to the outside of a cell of the methanol-utilizing bacterium. lysE24 encodes such a mutant LysE protein that does not have the wild-type loop region, or a mutant LysE protein that substantially consists only of the hydrophobic helixes.

The aforementioned mutant type LysE is not particularly limited so long as it has one or more hydrophobic helixes and promotes extracellular secretion of L-lysine, L-arginine or both of these L-amino acids when it is introduced into a methanol-utilizing bacterium. Specifically, a DNA coding for a mutant-type LysE that has all of the first to sixth hydrophobic helixes from the N-terminus is encompassed. More specifically, a DNA coding for a peptide containing the first to third hydrophobic helixes from the N-terminus, and a peptide containing the fourth to sixth hydrophobic helixes from the N-terminus is encompassed. The aforementioned lysE24 is an example of the mutant-type lysE that codes for a peptide containing the first to third hydrophobic helixes and a peptide containing the fourth to sixth hydrophobic helixes. The lysE24 gene results from introduction of a stop codon downstream from the region coding for the third hydrophobic helix. The inventors of the present invention confirmed that if the region downstream from this stop codon was deleted, the *Methylophilus methylotrophus* AS1 strain containing the lysE24 gene did not result in accumulation of L-lysine in the medium. Therefore, it was deducted that a peptide containing the first to third hydrophobic helixes and a peptide containing the fourth to sixth hydrophobic helixes are separately translated and function in a methanol-utilizing bacterium. Regardless, if the lysE24 gene is introduced into a methanol-utilizing bacterium, the amount of L-lysine or L-arginine produced will increase.

Any microorganisms can be utilized as the microorganism of origin for a DNA encoding a protein involved in secretion of L-lysine to outside of a cell, i.e., the lysE gene or its homologous gene, so long as the chosen microorganism has variants of the genes that can express the L-lysine secretion activity in a methanol-utilizing bacterium. Specifically, examples of such microorganisms include but are not limited to coryneform bacteria such as *Corynebacterium glutamicum* and *Brevibacterium lactofermentum, Escherichia* bacteria such as *Escherichia coli, Pseudomonas* bacteria such as *Pseudomonas aeruginosa, Mycobacterium* bacteria such as *Mycobacterium tuberculosis* and so forth.

When the amino acid secretion gene expression is enhanced in a methanol-utilizing bacterium, a recombinant DNA can be prepared by ligating its gene fragment to a vector functioning in methanol-utilizing bacterium, preferably a multi-copy type vector, and transformed into the methanol-utilizing bacterium. Alternatively, the gene can be incorporated into a transposon and introduced into chromosome. Furthermore, it is also possible to ligate a promoter upstream from the gene that induces strong transcription in a methanol-utilizing bacterium.

<3> Production of L-Amino Acid

An L-amino acid can be produced by culturing a methanol-utilizing bacterium having an ability to produce the L-amino acid obtained as described above in a medium to produce and accumulate the L-amino acid in culture and collecting the L-amino acid from the culture.

The microorganism used for the present invention can be cultured by a method typically used for culture of a methanol-utilizing microorganism. The medium used for the present invention may be either a natural or synthetic medium so long as it contains a carbon source, nitrogen source, inorganic ions and other trace amount organic components as required.

If methanol is used as a main carbon source, L-lysine or L-arginine can be produced at low cost. When methanol is used as a main carbon source, it is added to a medium in an amount of 0.001 to 30%. As the nitrogen source, ammonium sulfate or the like is used by adding it to the medium. Other than these, small amounts of the trace amount components such as potassium phosphate, sodium phosphate, magnesium sulfate, ferrous sulfate, manganese sulfate and so forth can be added.

The culture is performed under aerobic conditions with shaking, aeration by stirring, or the like, at a pH of 5 to 9 and a temperature of 20 to 45° C., and it is usually terminated within 24 to 120 hours.

Collection of L-lysine or L-arginine from culture can be typically attained by a combination of known methods, such as by use of an ion exchange resin, precipitation and other known methods.

EXAMPLES

Hereafter, the present invention will be explained more specifically with reference to the following examples.

The reagents used in the following examples were obtained from Wako Pure Chemicals or Nacalai Tesque unless otherwise indicated. The compositions of the media used in each example are shown below. pH was adjusted with NaOH or HCl for all of the media.

| LB medium: | |
|---|---|
| Trypton peptone (Difco) | 10 g/L |
| Yeast extract (Difco) | 5 g/L |
| Nacl | 10 g/L |
| pH 7.0 | |

These were steam-sterilized at 120° C. for 20 minutes.

| LB agar medium: | |
|---|---|
| LB medium | |
| Bacto agar | 15 g/L |

These were steam-sterilized at 120° C. for 20 minutes.

| SEII medium: | |
|---|---|
| K2HPO4 | 1.9 g/L |
| NaH2PO4 | 1.56 g/L |
| MgSO4.7H2O | 0.2 g/L |
| (NH4)2SO4 | 5 g/L |
| CuSO4.5H2O | 5 µg/L |
| MnSO4.5H2O | 25 µg/L |
| ZnSO4.7H2O | 23 µg/L |
| CaCl2.2H2O | 72 mg/L |
| FeCl3.6H2O | 9.7 mg/L |
| CaCO3 (Kanto Kagaku) | 30 g/L |
| Methanol | 2% (v/v) |
| pH 7.0 | |

The components other than methanol were subjected to steam sterilization at 121° C. for 15 minutes, and methanol was added after the medium was sufficiently cooled

| SEII agar medium: | |
|---|---|
| K2HPO4 | 1.9 g/L |
| NaH2PO4 | 1.56 g/L |
| MgSO4.7H2O | 0.2 g/L |
| (NH4)2SO4 | 5 g/L |
| CuSO4.5H2O | 5 µg/L |
| MnSO4.5H2O | 25 µg/L |
| ZnSO4.7H2O | 23 µg/L |
| CaCl2.2H2O | 72 mg/L |
| FeCl3.6H2O | 9.7 mg/L |
| Methanol | 0.5% (v/v) |
| pH 7.0 | |
| Bacto agar (Difco) | 15 g/L |

The components other than methanol were subjected to steam sterilization at 121° C. for 15 minutes, and methanol was added after the medium was sufficiently cool Example 1

<1> Cloning of Genes of Enzymes Constituting Entner-Doudoroff Pathway

The edd and eda gene, which code for enzymes EDD and EDA, respectively, a part of the Entner-Doudoroff pathway, have been cloned from *Escherichia coli*, *Zymomonas mobilis* and so forth. Since it is known that *Escherichia coli* genes can be expressed in the *Methylophilus methylotrophus* AS1 strain, it was decided to clone the edd and eda gene from *Escherichia coli*, and express them in a *Methylophilus* bacterium.

(1) Construction of Plasmid pMW-EDDA edd and eda form an operon in *Escherichia coli* (J. Bacteriol., 174 (14): 4638–46, July 1992), and it is possible to obtain using known techniques. Accordingly, edd-F (SEQ ID NO: 11) and eda-R (SEQ ID NO: 12) were designed as primers that would simultaneously amplify both the eda and edd genes when amplifying a DNA fragment which includes both genes by PCR using chromosomal DNA of the *E. coli* W3110 strain as a template. PCR was performed by using Pyrobest DNA Polymerase (Takara Shuzo), and it consisted of a reaction at 94° C. for 1 minute, followed by reactions at 94° C. for 30 seconds, 60° C. for 30 seconds and 72° C. for 3 minutes repeated for 30 cycles.

Subsequently, the obtained amplified fragment was completely digested with the restriction enzymes SalI and BamHI, ligated with plasmid pMW219 completely digested with the restriction enzymes SalI and BamHI and used to transform *Escherichia coli* JM109 (purchased from Takara Shuzo). The obtained colonies of transformants were inoculated into LB liquid medium containing 20 mg/L of kanamycin and cultured at 37° C. for 8 hours with shaking. Plasmid DNA was extracted from each culture broth by the alkali-SDS method, and structure of each plasmid was confirmed by digestion with restriction enzymes and determination of nucleotide sequence to obtain the target plasmid. This plasmid was designated as pMW-EDDA.

(2) Construction of Plasmid to be Used for Introducing edd and eda into *Methylophilus* Bacterium, pRSedda To introduce edd and eda into a *Methylophilus* bacterium, a known plasmid pRS was used to construct the pRSedda plasmid. pRS is a plasmid having the vector segment of the pVIC40 plasmid (International Patent Publication WO90/04636, International Patent Publication in Japanese (Kohyo) No. 3-501682) and obtained from pVIC40 by deleting a DNA region encoding the threonine operon contained in the plasmid. The plasmid pVIC40 is derived from a broad host spectrum vector plasmid pAYC32 (Chistorerdov, A. Y., Tsygankov, Y. D., Plasmid, 1986, 16, 161–167), which is a derivative of RSF1010.

Specifically, pRS was constructed as follows. The pVIC40 plasmid was digested with EcoRI and added to a phenol/chloroform solution, and mixed to terminate the reaction. After the reaction mixture was centrifuged, the upper layer was collected, and DNAs were collected by ethanol precipitation and separated on 0.8% agarose gel. A DNA fragment of about 8 kilobase pairs (henceforth abbreviated as "kbp") containing the vector side was collected by using EASY TRAP Ver. 2 (DNA collection kit, Takara Shuzo). The vector region fragment of the pVIC40 plasmid prepared as described above was self-ligated by using DNA Ligation Kit Ver. 2 (Takara Shuzo). This ligation reaction solution was used to transform *Escherichia coli* (*E. coli* JM109 competent cells, Takara Shuzo). The cells were applied on the LB agar medium containing 20 mg/L of streptomycin and incubated overnight at 37° C. The colonies that appeared on the agar medium were each inoculated to the LB liquid medium containing 20 mg/L of streptomycin and cultured at 37° C. for 8 hours with shaking. Plasmid DNA was extracted from each culture broth by the alkaline SDS method, and structure of each plasmid was confirmed by digestion with restriction enzymes to obtain pRS.

Then, a plasmid pRStac having the tac promoter was constructed from pRS according to the scheme shown in FIG. 1. The pRS vector was digested with the restriction enzymes EcoRI and PstI, added to a phenol/chloroform solution, and mixed to terminate the reaction. After the reaction mixture was centrifuged, the upper layer was collected, and DNAs were collected by ethanol precipitation and separated on 0.8% agarose gel. A DNA fragment of 8 kilobase pairs was collected by using EASY TRAP Ver. 2 (DNA collection kit, Takara Shuzo). The tac promoter region was amplified by PCR using the pKK223-3 plasmid (expression vector, Pharmacia) as a template and the primers shown in SEQ ID NOS: 1 and 2 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tac promoter was purified by using PCR prep (Promega) and then digested at the restriction enzyme sites preliminarily designed in the primers, i.e., at EcoRI and EcoT22I sites. Then, the reaction mixture was added with a phenol/chloroform solution and mixed with it to terminate the reaction. After the reaction mixture was centrifuged, the upper layer was collected and DNAs were collected by ethanol precipitation and separated on 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Shuzo). This ligation reaction solution was used to transform Escherichia coli (E. coli JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were identical to each other was selected as pRStac. The pRStac plasmid is a plasmid consisting of pRS inserted with the tac promoter as an apparatus for expressing the genes.

Subsequently, pRStac mentioned above was digested with Sse8387I (Takara Shuzo) and SapI (New England Biolabs), added to a phenol/chloroform solution, and mixed to terminate the reaction. After the reaction mixture was centrifuged, the upper layer was collected, and DNAs were collected by ethanol precipitation and separated on 0.8% agarose gel to obtain a DNA fragment of about 8.0 kbp. Then, pMW-EDDA constructed in (1) mentioned above was digested with the restriction enzymes SalI and BamHI, added with a phenol/chloroform solution and mixed with it to terminate the reaction. After the reaction mixture was centrifuged, the upper layer was collected, and DNAs were collected by ethanol precipitation and separated on 0.8% agarose gel to obtain a DNA fragment of about 2.9 kbp.

The digestion product of the pRStac vector and the edd and eda gene region fragment prepared as described above were ligated by using DNA Ligation Kit Ver. 2 (Takara Shuzo). This ligation reaction solution was used to transform Escherichia coli (E. coli JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method, and structure of each plasmid was confirmed by digestion with restriction enzymes and determination of nucleotide sequence to obtain the target plasmid. This plasmid was designated as pRSedda. In pRSedda, the edd and eda genes were positioned so that their transcription directions should be the same as that of the tac promoter.

<2> Construction of L-Lysine Producing Bacterium from *Methylophilus* Bacterium

In order to investigate the effect of pRSedda plasmid on L-lysine production, pBBR-lysEdapA plasmid was constructed, which can coexist with a vector derived from pRS and enables amplification of genes coding for a protein having L-lysine secretion activity and the DDPS enzyme.

(1) Construction of pRSlysE

An lysE gene, which was a homologous gene of the gene facilitating secretion of L-lysine known for *Corynebacterium glutamicum* R127 (Vrljic M., Sahm H., Eggeling L., Molecular Microbiology 22:815–826 (1996)) was cloned from a *Brevibacterium lactofermentum* 2256 strain, and it was attempted to express it in a *Methylophilus* bacterium.

pRStac obtained as described above was digested with Sse8387I (Takara Shuzo) and SapI (New England Biolabs), added to a phenol/chloroform solution, and mixed to terminate the reaction. After the reaction mixture was centrifuged, the upper layer was collected, and DNAs were collected by ethanol precipitation and separated on 0.8% agarose gel to obtain a DNA fragment of about 9.0 kbp.

The lysE gene fragment was amplified by PCR using the chromosome extracted from *Brevibacterium lactofermentum* 2256 strain (ATCC13869) as a template and the primers shown in SEQ ID NOS: 5 and 6 (denaturation at 94° C. for 20 seconds, annealing at 55° C. for 30 seconds and extension reaction at 72° C. for 90 seconds). Pyrobest DNA polymerase (Takara Shuzo) was used for PCR. In the above amplification, in order that expression of the lysE gene should become possible in a *Methylophilus* bacterium, the primers were designed so that nucleotides of 9 to 15 bp from the translation initiation codon of the lysE gene should be replaced with a sequence that is known to function in a *Methylophilus* bacterium (Wyborn, N. R., Mills, J., Williamis, S. G. and Jones, C. W., Eur. J. Biochem., 240, 314–322 (1996)). The obtained fragment was purified by using PCR prep (Promega) and then digested with the restriction enzymes Sse8387I and SapI. The reaction mixture was added to a phenol/chloroform solution and mixed to terminate the reaction. After the reaction mixture was centrifuged, the upper layer was collected and DNAs were extracted by ethanol precipitation and collected from a 0.8% agarose gel.

The digestion product of the pRStac vector and the lysE gene region fragment prepared as described above were ligated by using DNA Ligation Kit Ver. 2 (Takara Shuzo). This ligation reaction solution was used to transform Escherichia coli (E. coli JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain pRSlysE (FIG. 1). In pRSlysE, the lysE gene was positioned so that its transcription direction should be the same as that of the tac promoter.

(2) Introduction of pRSlysE into *Methylophilus* Bacterium pRSlysE obtained as described above was introduced into *Methylophilus methylotrophus* AS1 strain (NCIMB10515) by electroporation (Canadian Journal of Microbiology, 43, 197 (1997)). In addition, pRS was introduced into the AS1 strain as a control in the same manner as that for pRSlysE. As a result, several thousands of colonies were obtained per 1 µg of DNA with pRS used as a control, whereas only several colonies were obtained with pRSlysE.

When plasmids were extracted from transformant strains thought to contain pRSlysE and their nucleotide sequences were investigated, a spontaneous mutation was discovered in a region encoding lysE for all the investigated plasmids, and in some cases, a nonsense mutation was discovered as the mutation, by which a codon encoding an amino acid was replaced with a stop codon that terminated the translation. In other plasmids, deletion was observed in the lysE gene. It was thought that, in either case, the function of lysE was lost.

As described above, the introduction frequency of pRSlysE carrying the full length lysE gene into *Methylophilus methylotrophus* was extremely low, and only plasmids having a lysE mutant gene whereby the mutation eliminated the function could be introduced. Considering these facts in combination, it was thought that the introduction of the lysE gene into *Methylophilus methylotrophus* was lethal. This indicates that the lysE gene cannot universally function for the secretion of L-lysine in heterogenous bacteria.

The *Methylophilus methylotrophus* AS1 strain containing pRSlysE having a mutation was applied to an SEII plate containing 50 mg/L of streptomycin and cultured overnight at 37° C. Then, the cells on about 10 cm2 of the medium surface were scraped, inoculated into SEII production medium (20 ml) containing 50 mg/L of streptomycin, and cultured at 37° C. for 34 hours with shaking. After completion of the culture, the cells were removed by centrifugation, and the L-lysine concentration in the culture supernatant was determined by using an amino acid analyzer (Nihon Bunko, high speed liquid chromatography). As a result, substantially no strain was obtained in which secretion of L-lysine was enhanced in spite of the introduction of the mutant lysE gene.

(3) Acquisition of Gene Providing L-Lysine Secretion Activity in *Methylophilus* Bacteria As described in the preceding section, it was suggested that the known lysE gene is lethal in *Methylophilus* bacteria, and resulted in many mutant non-functional genes.

However, during analysis of most of pRSlysE introduced with a mutation, a mutant lysE gene that functioned in *Methylophilus* bacteria was obtained.

This mutant lysE gene was designated as lysE24 gene. When the nucleotide sequence of lysE24 gene was analyzed, it was found that this mutation was not a mutation resulting in an amino acid substitution, but a nonsense mutation introducing a stop codon around the center of the translation region of lysE.

The result of nucleotide sequence determination of lysE24 is shown in SEQ ID NO: 9. The nucleotide sequence of wild-type lysE of *Brevibacterium lactofermentum* is shown in SEQ ID NO: 7 for comparison. In lysE24, T (thymine) was inserted after G (guanine) at the 355th position, resulting in the sequence shown in SEQ ID NO: 9. The plasmid containing lysE24 was designated as pRSlysE24 (FIG. 1).

The *E. coli* JM109 strain transformed with pRSlysE24 was designated as AJ13830, and this strain was deposited at the independent administrative corporation, National Institute of Advanced Industrial Science and Technology, International Patent Organism Depositary, AIST Tsukuba Central 6, 1-1, Higashi 1-Chome Tsukuba-shi, Ibaraki-ken 305-8566, Japan on Jun. 4, 2001 and received an accession number of FERM P-18369. Then, the deposit was converted to an international deposit under the provisions of the Budapest Treaty on May 13, 2002, and received accession number FERM BP-8040.

It was found that when the lysE24 gene was introduced into the *Methylophilus methylotrophus* AS1 strain, L-lysine accumulated in the medium. It was thought that this was caused by enhancement of the secretion of L-lysine.

(4) Construction of Plasmid pRSdapA Having dapA* Gene

A plasmid was prepared having a gene (dapA*) encoding dihydrodipicolinate synthase that was not subject to feedback inhibition by L-lysine as an L-lysine biosynthesis system enzyme gene.

pRStac was digested with Sse8387I and XbaI, added to a phenol/chloroform solution, and mixed to terminate the reaction. After the reaction mixture was centrifuged, the upper layer was collected, and DNA were collected by ethanol precipitation and separated on 0.8% agarose gel to collect a DNA fragment of about 9 kbp.

The known plasmid RSFD80 (see WO90/16042) containing the dapA* gene fragment was used as a template to amplify dapA* via PCR using the primers shown in SEQ ID NOS: 3 and 4 (denaturation at 94° C. for 20 seconds, annealing at 55° C. for 30 seconds and extension reaction at 72° C. for 60 seconds). Pyrobest DNA polymerase (Takara Shuzo) was used for PCR. The obtained dapA* fragment was purified by using PCR prep (Promega) and then digested with the restriction enzymes Sse8387I and XbaI. The reaction mixture was added to a phenol/chloroform solution and mixed to terminate the reaction. After the reaction mixture was centrifuged, the upper layer was collected and DNA were collected by ethanol precipitation and separated on 0.8% agarose gel to collect a DNA fragment of about 0.1 kbp.

The digestion product of the pRStac vector and the dapA* gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain a pRSdapA plasmid. In the pRSdapA plasmid, the dapA* gene was positioned so that its transcription direction should be the same as that of the tac promoter.

(5) Construction of Plasmid Having lysE24 and dapA*

Figure 2:
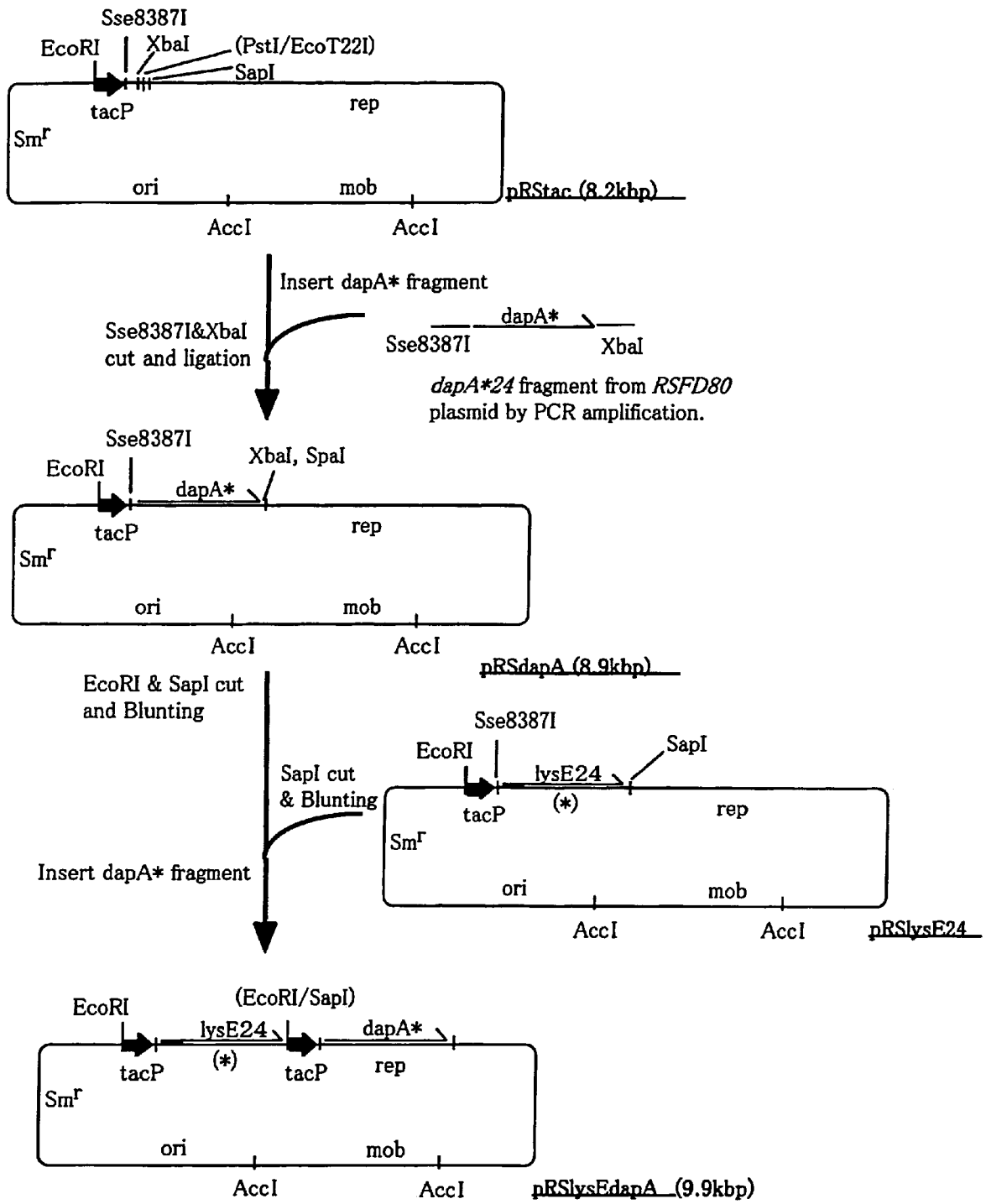
FIG. 2 shows construction of a plasmid pRSlysEdapA having the lysE24 gene and dapA* gene.

In order to evaluate effect of combination of lysE24 and dapA*, a plasmid consisting of the pRSlysE plasmid inserted with the dapA* gene was constructed in the scheme shown in FIG. 2. pRSlysE24 prepared in the above (3) was digested with the restriction enzyme SapI and ends of the product were blunt-ended by using DNA Blunting Kit (Takara Shuzo). Furthermore, the plasmid pRSdapA prepared in the above (4) was digested with restriction enzymes EcoRI and SapI, and a fragment of about 1 kbp containing the tac promoter and the dapA* region was separated on 0.8% agarose gel and collected by using EASY TRAP Ver 2 (Takara Shuzo). This fragment was blunt-ended in the same manner as described above and ligated to the aforementioned digestion product of pRSlysE24 by using DNA Ligation Kit Ver 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain a pRSlysEdapA plasmid. In this plasmid, the lysE24 gene and the dapA* gene were positioned so that their transcription directions should be identical to each other.

The *E. coli* JM109 strain transformed with the pRSlys EdapA plasmid was designated as AJ13832, and this strain was deposited at the independent administrative corporation, National Institute of Advanced Industrial Science and Technology, International Patent Organism Depositary on Jun. 4, 2001 and received an accession number of FERM P-18371. Then, the deposit was converted to an international deposit under the provisions of the Budapest Treaty on May 13, 2002, and received an accession number of FERM BP-8042.

(6) Construction of Plasmid that can Coexist with pRS Vector, pBBR-lysEdapA

Then, pBBR-lysEdapA was prepared from pRSlysEdapA.

It is known that the pBBR1 plasmid can replicate in the *Methylophilus methylotrophus* AS1 strain, and can coexist with the pRS vector (Canadian Journal of Microbiology, 43. 197 (1997); MoBiTec GmbH, Lotzestrasse 22a 37083 Gottingen Germany, it can be purchased from Funakoshi). First, pBBR1 was digested with DraI, and added to a phenol/chloroform solution, and mixed toterminate the reaction. After the reaction mixture was centrifuged, the upper layer was collected, and DNAs were collected by ethanol precipitation and separated on 0.8% agarose gel to collect a DNA fragment of about 5.3 kbp.

Then, the pRSlysEdapA plasmid constructed in section (5) mentioned above was digested with EcoRI and BglII, and added to a phenol/chloroform solution, and mixed to terminate the reaction. After the reaction mixture was centrifuged, the upper layer was collected, and DNAs were collected by ethanol precipitation and separated on 0.8% agarose gel to collect a DNA fragment of about 2.0 kbp containing the lysE24 and dapA genes.

The pBBR1 vector digestion product and the DNA fragment containing the lysE24 and dapA gene regions prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of kanamycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method, and structure of each plasmid was confirmed by digestion with restriction enzymes and determination of nucleotide sequence to obtain pBBR-lysEdapA.

The pBBR-lysEdapA plasmid obtained as described above was introduced into *Methylophilus methylotrophus* AS1 strain by electroporation (Canadian Journal of Microbiology, 43, 197 (1997)). In addition, pBBR1 was also introduced into the AS1 strain as a control in the same manner as that for pBBR-lysEdapA.

<3> Production of L-Lysine Using Entner-Doudoroff Pathway-Enhanced Strain

L-lysine producing ability was evaluated by introducing the pRSedda plasmid into the *Methylophilus methylotrophus* AS1 strain harboring the pBBR-lysEdapA plasmid obtained as described above (also referred to with an abbreviation of AS1/pBBR-lysEdapA) by electroporation. The obtained transformant strain (henceforth also referred to as "AS1/PBBR-lysEdapA/pRSedda") and the *Methylophilus* methylotrophusAS1/pBBR-lysEdapA strain introduced with the pRS plasmid (henceforth also referred to as "AS1/pBBR-lysEdapA/pRS") as a control were investigated for intracellular L-amino acid concentrations and L-amino acid concentrations in culture supernatant.

Each transformant strain was cultured overnight at 37° C. on an SEII plate containing 50 mg/L of streptomycin and 50 mg/L of kanamycin. Then, the cells of about 10 cm2 of the medium surface were scraped, inoculated into SEII production medium (20 ml) containing 50 mg/L of streptomycin and 50 mg/L of kanamycin, and cultured at 37° C. for 48 hours with shaking. After completion of the culture, the cells were removed by centrifugation from a part of the culture broth, and the L-amino acid concentrations in the culture supernatant were determined by using an amino acid analyzer (Nihon Bunko, high speed liquid chromatography).

The results are shown in Table 1. AS1/pBBR-lysEdapA/pRSedda accumulated L-lysine in the medium at a higher concentration compared with AS1/pBBR-lysEdapA/pRS, and thus it can be seen that the L-lysine productivity was improved by the enhancement of the edd and eda genes.

TABLE 1

| Bacterial strain | L-Lysine concentration in culture supernatant (g/L) |
| --- | --- |
| AS1/pBBR-lysEdapA/pRS | 1.15 |
| AS1/pBBR-lysEdapA/pRSedda | 1.35 |

As described above, these results demonstrate that the L-lysine productivity can be improved by the enhancement of the expression of the genes of the Entner-Doudoroff pathway.

<4> Production of L-Valine Using Entner-Doudoroff Pathway-Enhanced Strain pRSedda obtained as described above was introduced into the wild-type *Methylophilus methylotrophus* AS1 strain by electroporation (Canadian Journal of Microbiology, 43, 197 (1997)). In addition, pRS was also introduced into the AS1 strain in the same manner as a control.

The obtained transformant strain (henceforth also referred to as "AS1/pRSedda") and the *Methylophilus methylotrophus* strain introduced with the pRS plasmid (henceforth also referred to as "AS1/pRS") as a control were investigated for intracellular L-amino acid concentrations and L-amino acid concentrations in culture supernatant.

Each transformant strain was cultured overnight at 37° C. on an SEII plate containing 50 mg/L of streptomycin. Then, the cells of about 10 cm2 of the medium surface were scraped, inoculated into SEII production medium (20 ml) containing 50 mg/L of streptomycin, and cultured at 37° C. for 48 hours with shaking. After completion of the culture, the cells were removed by centrifugation from a part of the culture broth, and the L-amino acid concentrations in the culture supernatant were determined by using an amino acid analyzer.

The results are shown in Table 2. L-valine accumulated in the medium containing AS1/pRSedda at a higher concentration compared with AS1/pRS, and thus it can be seen that the L-valine productivity was improved by the enhancement of the edd and eda genes.

TABLE 2

| Bacterial strain | L-Valine concentration in culture supernatant (g/L) |
|---|---|
| AS1/pRS | 0.01 |
| AS1/pRSedda | 0.20 |

As described above, these results demonstrate that the L-valine producing ability can be improved by the enhancement of expression of the genes of the Entner-Doudoroff pathway.

<5> Investigation of Ability to Produce Other L-Amino Acids with the Entner-Doudoroff Pathway-Enhanced Strain AS1/pRSedda and AS1/pRS were each cultured overnight at 37° C. on an SEII plate containing 50 mg/L of streptomycin. Then, the cells of about 10 cm2 of the medium surface were scraped, inoculated into SEII production medium (20 ml) containing 50 mg/L of streptomycin, and cultured at 37° C. for 48 hours with shaking. After completion of the culture, the cells were removed by centrifugation from a part of the culture broth, and the L-amino acid concentrations in the culture supernatant were determined by using an amino acid analyzer.

The results are shown in Table 3. All of the L-amino acids accumulated in the medium containing AS1/pRSedda at higher concentrations when compared with AS1/pRS, and thus it can be seen that the productivities of various L-amino acid were improved by the enhancement of expression of the edd and eda genes. In particular, other than L-valine in the above section (4), the productivities of L-leucine and L-isoleucine were markedly improved.

TABLE 3

| | L-Amino acid concentration in culture supernatant (mg/L) | |
|---|---|---|
| L-Amino acid | AS1/pRS | AS1/pRSedda |
| L-Aspartic acid | 0 | 2 |
| L-Threonine | 9.4 | 18.6 |
| L-Serine | 1.8 | 2 |
| L-Glutamic acid | 35.9 | 46.8 |
| Glycine | 4.5 | 6.4 |
| L-Alanine | 16.7 | 37.9 |
| L-Valine | 10.2 | 202.3 |
| L-Isoleucine | 9.5 | 100.1 |
| L-Leucine | 10.8 | 53.8 |
| L-Tyrosine | 8.4 | 9.7 |
| L-Phenylalanine | 18.4 | 20.9 |
| L-Lysine | 6.4 | 8 |
| L-Arginine | 3.6 | 4 |

As described above, it was demonstrated that the productivities of the various L-amino acids could be improved by the enhancement of expression of the genes of the Entner-Doudoroff pathway.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2002336346, is incorporated by reference herein in its entirety.

The invention claimed is:

1. A method for producing an L-amino acid comprising:
a) culturing a microorganism having the ability to produce said L-amino acid in a medium, whereby said L-amino acid accumulates in the medium, and
b) collecting said L-amino acid from the medium,
wherein said microorganism is a methanol-utilizing bacterium having the Entner-Doudoroff pathway and is modified so that 6-phosphogluconate dehydratase activity and/or 2-keto-3-deoxy-6-phosphogluconate aldolase activity are/is enhanced as compared to a wild-type bacterium, and said L-amino acid is selected from L-amino acids produced by a biosynthetic pathway which utilizes pyruvic acid as an intermediate, wherein said 6-phosphogluconate dehydratase activity is enhanced by
A) increasing the copy number of a gene coding for 6-phosphogluconate dehydratase as compared to a wild-type bacterium, or
B) replacing the native promoter of said gene with a stronger promoter so that expression of the gene is enhanced in said bacterium as compared to a wild-type bacterium, and
wherein said 2-keto-3-deoxy-6-phosphogluconate aldolase activity is enhanced by
C) increasing the copy number of a gene coding for 2-keto-3-deoxy-6-phosphogluconate aldolase as compared to a wild-type bacterium, or
D) replacing the native promoter of said gene with a stronger promoter so that expression of the gene is enhanced in said bacterium as compared to a wild-type bacterium.

2. The method of claim 1, wherein said methanol-utilizing bacterium comprises a bacterium belonging to the genus *Methylophilus*.

3. The method of claim 1, wherein said L-amino acid is selected from the group consisting of L-lysine, L-leucine, L-isoleucine and L-valine.

4. A methanol-utilizing bacterium having the Entner-Doudoroff pathway, whereby said bacterium is modified so that 6-phosphogluconate dehydratase activity and/or 2-keto-3-deoxy-d-phosphogluconate aldolase activity are/is enhanced, and has the ability to produce an L-amino acid via a biosynthetic pathway which utilizes pyruvic acid as an intermediate.

5. A method for producing an L-amino acid which is a product of a biosynthetic pathway which utilizes pyruvic acid as an intermediate comprising:

a) culturing a methanol-utilizing bacterium having the Entner-Doudoroff pathway in a medium, wherein said bacterium has the ability to secrete said L-amino acid into a medium, b) collecting said L-amino acid from the medium, wherein said bacterium is modified to enhance 6-phosphogluconate dehydratase activity and/or 2-keto-3-deoxy-6-phosphogluconate aldolase activity, as compared to a wild-type bacterium, wherein said 6-phosphogluconate dehydratase activity is enhanced by A) increasing the copy number of a gene coding for 6-phosphogluconate dehydratase as compared to a wild-type bacterium, or B) replacing the native promoter of said gene with a stronger promoter so that expression of the gene is enhanced in said bacterium as compared to a wild-type bacterium, and wherein said 2-keto-3-deoxy-6-phosphogluconate aldolase activity is enhanced by C) increasing the copy number of a gene coding for 2-keto-3-deoxy-6-phosphogluconate aldolase as compared to a wild-type bacterium, or D) replacing the native promoter of said gene with a stronger promoter so that expression of the gene is enhanced in said bacterium as compared to a wild-type bacterium.

6. The method of claim 5, wherein said methanol-utilizing bacterium comprises a bacterium belonging to the genus *Methylophilus*.

7. The method of claim 5, wherein said L-amino acid is selected from the group consisting of L-lysine, L-leucine, L-isoleucine and L-valine.

* * * * *